US 6,453,904 B1

(12) United States Patent
Wilson et al.

(10) Patent No.: US 6,453,904 B1
(45) Date of Patent: Sep. 24, 2002

(54) ARM-SLING VEST

(76) Inventors: Greg W. Wilson, 103 Barstow Pl., Lawrence, KS (US) 66049; Cinda J. Lewis, 2501 N. Estates Dr., Arkansas City, KS (US) 67005

( * ) Notice: Subject to any disclaimer, the term of this patent is extended or adjusted under 35 U.S.C. 154(b) by 0 days.

(21) Appl. No.: 10/101,233

(22) Filed: Mar. 19, 2002

(51) Int. Cl.[7] ................................................ A61F 5/37
(52) U.S. Cl. ........................................ 128/874; 602/4
(58) Field of Search ......................... 602/4, 5, 62; 2/44, 2/45; 128/845, 846, 869, 874, 875, 877, 878, 879, DIG. 15

(56) References Cited

U.S. PATENT DOCUMENTS

| | | | | |
|---|---|---|---|---|
| 1,266,688 A | * | 5/1918 | Kassner | ........................ 602/4 |
| 1,621,323 A | * | 3/1927 | Horn | ............................ 602/4 |
| 2,560,243 A | * | 7/1951 | Peterson | |
| 3,559,640 A | | 2/1971 | Beckett | |
| 3,780,729 A | * | 12/1973 | Gurnett | ....................... 128/94 |
| 4,550,724 A | | 11/1985 | Berrehail | |
| 4,601,285 A | | 7/1986 | Whitchurch | |
| 4,733,658 A | | 3/1988 | Ruthven, Jr. | |
| 4,751,923 A | * | 6/1988 | Marino | .......................... 602/4 |
| 4,878,490 A | | 11/1989 | Gross | |
| 5,095,894 A | | 3/1992 | Marble | |
| 5,358,470 A | | 10/1994 | Johnson | |

* cited by examiner

*Primary Examiner*—Michael A. Brown
(74) *Attorney, Agent, or Firm*—Dale J. Ream

(57) ABSTRACT

An arm-sling vest includes sleeveless front and back vest panels defining an opening permitting the panels to fit over a person's head so as to rest upon the shoulders. Lateral edges of the panels include hook and loop fasteners for releasably and adjustably connecting the panels together about a person's torso. A pair of support straps are attached to an outer surface of the front vest panel and include free ends extending therefrom. A corresponding pair of retainer patches are attached to the front vest panel and positioned above the support straps and aligned therewith, respectively. The support straps and retainer patches include complementary fasteners such that the straps may cradle a person's forearm and secured to a respective retainer patch. The support straps are independently operable such that a person's forearm may be cradled in a plurality of orientations.

16 Claims, 5 Drawing Sheets

ARM-SLING VEST

BACKGROUND OF THE INVENTION

This invention relates generally to an orthopedic vest and, more particularly, to an orthopedic vest that supports and restrains a person's arm and does not subject the person to neck or back strain.

A person who has suffered a dislocated shoulder, has suffered a broken arm, wrist, etc., or has undergone surgery related to such medical conditions must take great care to keep the affected joint or limb as immobilized as possible for a period of time so as to promote proper healing. Various devices have been proposed in the art for stabilizing an arm or shoulder, such as those slings or devices shown in U.S. Pat. Nos. 3,559,640, 4,878,490, and 5,095,894. Although assumably effective for their intended purposes, the existing devices do not provide a vest that is easy to put on, remove, and adjust by the wearer as needed.

Therefore, it is desirable to have an arm-sling vest that is easy to slip on or off without requiring an affected arm to be threaded into a cradle element. Further, it is desirable to have an arm-sling vest in which the wearer may easily adjust the orientation of their arm at any time. In addition, it is desirable to have an arm-sling vest that is adjustable by the wearer to accommodate persons of different size or as personal comfort dictates.

SUMMARY OF THE INVENTION

An arm-sling vest according to the present invention provides front and back vest panels that are essentially coextensive and integrally constructed at an upper end with each panel including a free edge opposite the upper end. The front and back vest panels define an opening at the upper end that permits the panels to be inserted over a person's head and rest upon the person's shoulders. The arm-sling vest is sleeveless and the front and back vest panels substantially cover a person's torso when fitted over the person's head. The front and back vest panels include hook and loop material adjacent the free edges thereof such that the panels may easily be releasably connected together or released by the wearer. This also enables the wearer to easily readjust the fit of the arm-sling vest during wear, as comfort preferences may dictate.

The arm-sling vest includes a pair of spaced apart straps attached to the front vest panel. A corresponding pair of retainer patches are also attached to the front vest panel at positions upwardly adjacent to the respective strap attachments. The straps and retainer patches also include hook and loop fasteners such that the straps may be wrapped about the wearer's arm and then secured to a respective patch. As the straps are separate and independent, one strap may, for example, be positioned to allow a portion of a person's arm to droop while the other strap may be positioned to cause another portion of the arm to be raised. This allows an arm to be held in a plurality of configurations and such configurations may be modified by the wearer easily and by using only one hand.

Therefore, a general object of this invention is to provide an arm-sling vest for immobilizing and stabilizing a person's shoulder, arm, wrist, or the like.

Another object of this invention is to provide an arm-sling vest, as aforesaid, which is easy for a user to put on and take off without assistance.

Still another object of this invention is to provide an arm-sling vest, as aforesaid, that is adjustable for use by persons of different sizes.

Yet another object of this invention is to provide an arm-sling vest, as aforesaid, that may be laundered in a conventional manner.

A further object of this invention is to provide an arm-sling vest, as aforesaid, which may be used to support either of a person's arms without changing the vest's configuration.

A still further object of this invention is to provide an arm-sling vest, as aforesaid, which enables the wearer to adjust the angle at which his arm is supported.

Other objects and advantages of this invention will become apparent from the following description taken in connection with the accompanying drawings, wherein is set forth by way of illustration and example, embodiments of this invention.

DESCRIPTION OF THE PREFERRED EMBODIMENT

Figure 1:
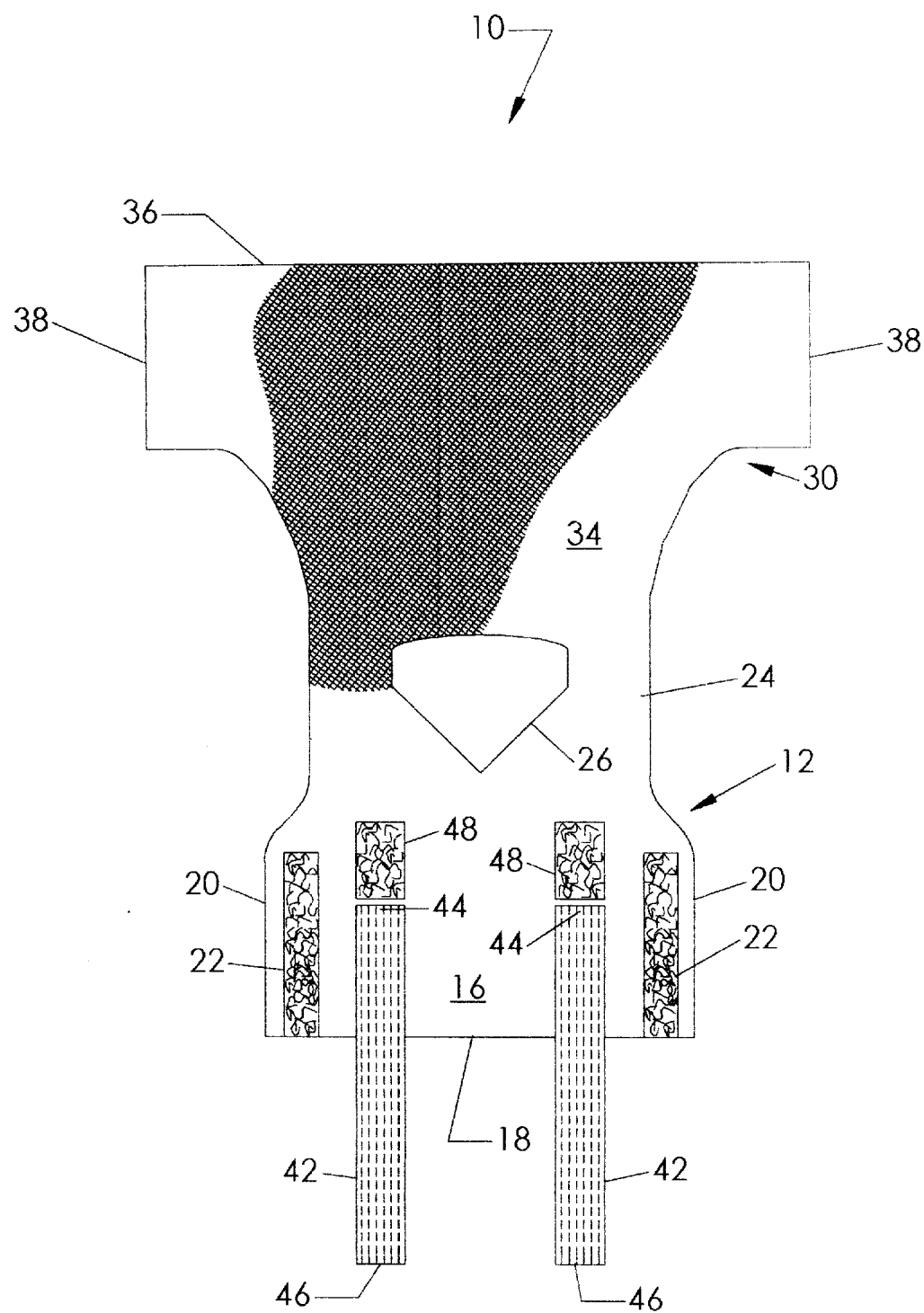
FIG. 1 is a plan view of the outside of an arm-sling vest according to one embodiment of the present invention.
Figure 2:
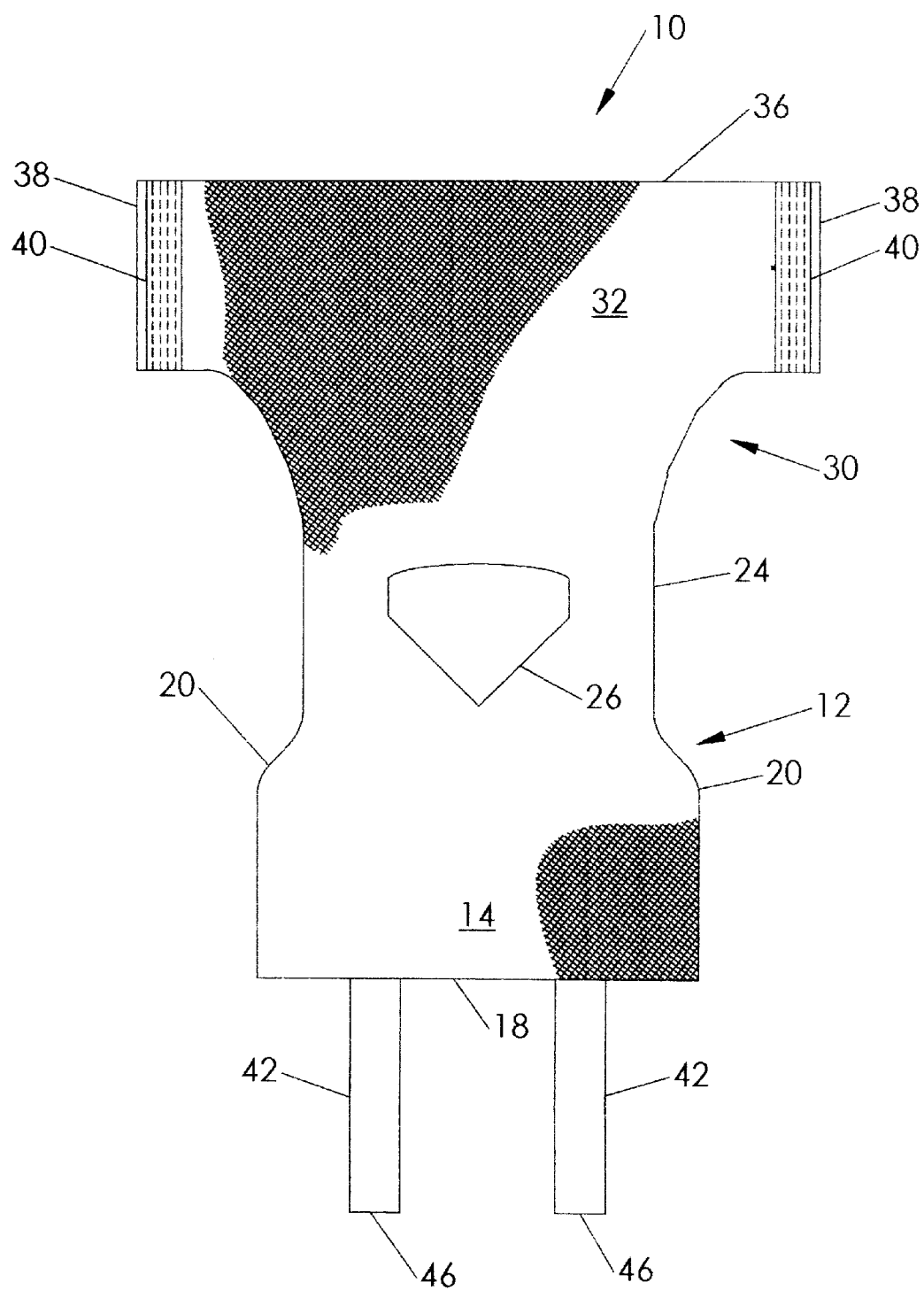
FIG. 2 is a plan view of the inside of the arm-sling vest as in FIG. 1.

An arm-sling vest according to the present invention will now be described in detail with reference to FIGS. 1 through 5 of the accompanying drawings. An arm-sling vest according to one embodiment of the present invention is shown in FIGS. 1, 2, and 5 and includes a front vest panel 12 and back vest panel 30. The front vest panel 12 includes opposed inner 14 and outer 16 surfaces. Similarly, the back vest panel 30 includes inner 32 and outer 34 surfaces. The front vest panel 12 is essentially coextensive with the back vest panel 30. More particularly, the front 12 and back 30 vest panels are connected at an upper end 24 of the arm-sling vest 10 and present free edges 18, 36, respectively, opposite the upper end 24 (FIG. 1). The front 12 and back 30 vest panels are constructed of a material that may be conventionally laundered without damage, such as cotton although a nylon or other materials would also work.

At the upper end 24, the front 12 and back 30 vest panels define an opening 26 suitable to permit the front 12 and back 30 vest panels to be fitted over the head of a person and to be supported upon the shoulders of the person. Relative to the back vest panel 30, the head opening 26 presents a downwardly annular edge that approximates the configuration of the back of a wearer's neck. Relative to the front vest panel 12, the opening 26 presents a V-shaped configuration such that an upper portion of the front vest panel does not constrict or provide discomfort to the front of a wearer's neck in use. Other opening configurations not shown or described would also be suitable so long as they do not inhibit the wearer's ease in fitting the panels over his head or cause discomfort in use.

The back vest panel 30 includes a pair of wing sections 38 integrally connected to laterally opposed side edges thereof and adjacent the back vest panel free edge 36 (FIGS. 1 and 2). The back wing sections 38 extend only partially toward the upper end 24 such that the arm-sling vest 10 remains sleeveless and the wearer need not thread his arms through sleeves, pouches, or the like. A pair of connector strips 40 are fixedly attached to the inner surface 32 of respective back wing sections 38 along lateral edges thereof (FIG. 2). Preferably, each connector strip 40 includes one of a hook and loop fastening material, such as Velcro.

The front vest panel 12 also includes a pair of wing sections 20 integrally connected to laterally opposed side edges thereof and adjacent the front vest panel free edge 18. A pair of complementary connector strips 22 are fixedly attached to the outer surface 16 of respective front wing sections 20 along lateral edges thereof (FIG. 1). It is understood that the front wing sections 20 preferably do not extend laterally as far as the rear wing sections although such a configuration would also work. Preferably, each complementary connector strip 22 includes another of the hook and loop fastening material, such as Velcro. In other words, if the connector strips 40 include hook fasteners, then the complementary connector strips 22 include loop fasteners, and vice versa. Of course, other fastening materials would also work, such as snaps, button/button hole combinations, magnet/metallic element combinations, and the like. It is also understood that while the connector strips are preferably mounted parallel to the lateral edges of the front 12 and back 30 panels, other configurations would also be suitable.

The arm-sling vest 10 further includes a pair of elongate support straps 42 (FIG. 1), each support strap having opposed first 44 and second 46 ends. The first end 44 of each support strap 42 is fixedly attached to the outer surface 16 of the front vest panel 12. The pair of support straps 42 are laterally spaced from and parallel to one another, the first ends 44 being equally displaced from the free edge 18 of the front vest panel 12. Each support strap 42 establishes an imaginary longitudinal axis normal to the free edge 18 of the front vest panel 12. The second ends 46 of the support straps 42 hang below the free edge 18 when the arm-sling vest 10 is being worn. An outer surface of each support strap 42 includes one of a hook and loop fastening material, such as Velcro.

A pair of laterally spaced apart retainer patches 48 are fixedly attached to the outer surface 16 of the front vest panel 12 (FIG. 1). Each retainer patch 48 is displaced from a first end 44 of a respective strap 42 and positioned between said respective first end 44 and the opening 26 and aligned along a respective imaginary longitudinal axis (FIG. 1). Each retainer patch 48 further includes another of a hook and loop fastening material relative to the one of a hook and loop fastening material of a respective support strap 42. In other words, if the support straps include hook fastening material, then the retainer patches 48 include loop fastening material and vice versa. Of course, other fastening material may be used, such as snaps, magnet/metallic element combinations, button/button hole combinations, and the like.

In use, a person may manipulate the integrally connected front 12 and back 30 vest panels using a single hand such that the person's head is inserted through the opening and such that the upper end 24 rests upon the person's shoulders. This allows the front vest panel 12 to extend over the wearer's chest and frontal torso and allows the back vest panel to extend over the wearer's back. Again using a single hand, the wearer may, in turn, wrap the back wing sections 38 around his torso so as to be coupled with corresponding front wing sections 20 (FIG. 5). The wearer may wrap the wing sections as tight or loose as desired. The wearer may then position the forearm to be cradled at a desired inclination between the front free edge 18 and the retainer patches 48. The support straps 42 may be extended over the arm to be cradled and the fasteners of the respective straps and patches may be engaged. The elongate support straps 42 may completely encircle the arm prior to coupling to a patch, if need be. Therefore, one strap may be secured with a great deal of slack so as to allow one portion of the arm to droop while the other strap may include virtually no slack so as to hold another portion of the arm in a raised configuration. Each support strap 42 may be operated individually such that the wearer is able to re-orient the cradled forearm using only one hand and without assistance.

Figure 3:
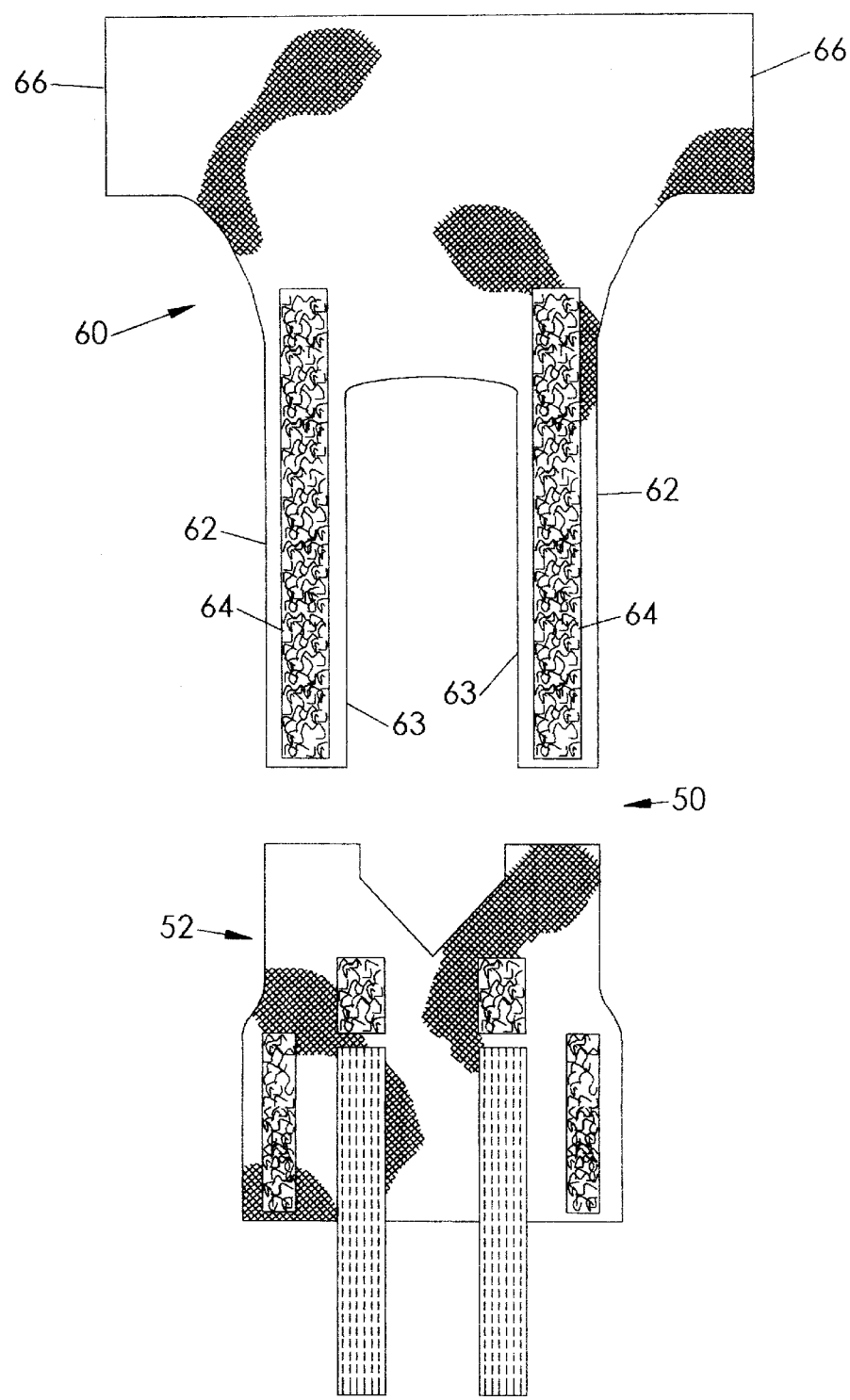
FIG. 3 is a plan view of the outside of an arm-sling vest according to another embodiment of the invention.
Figure 4:
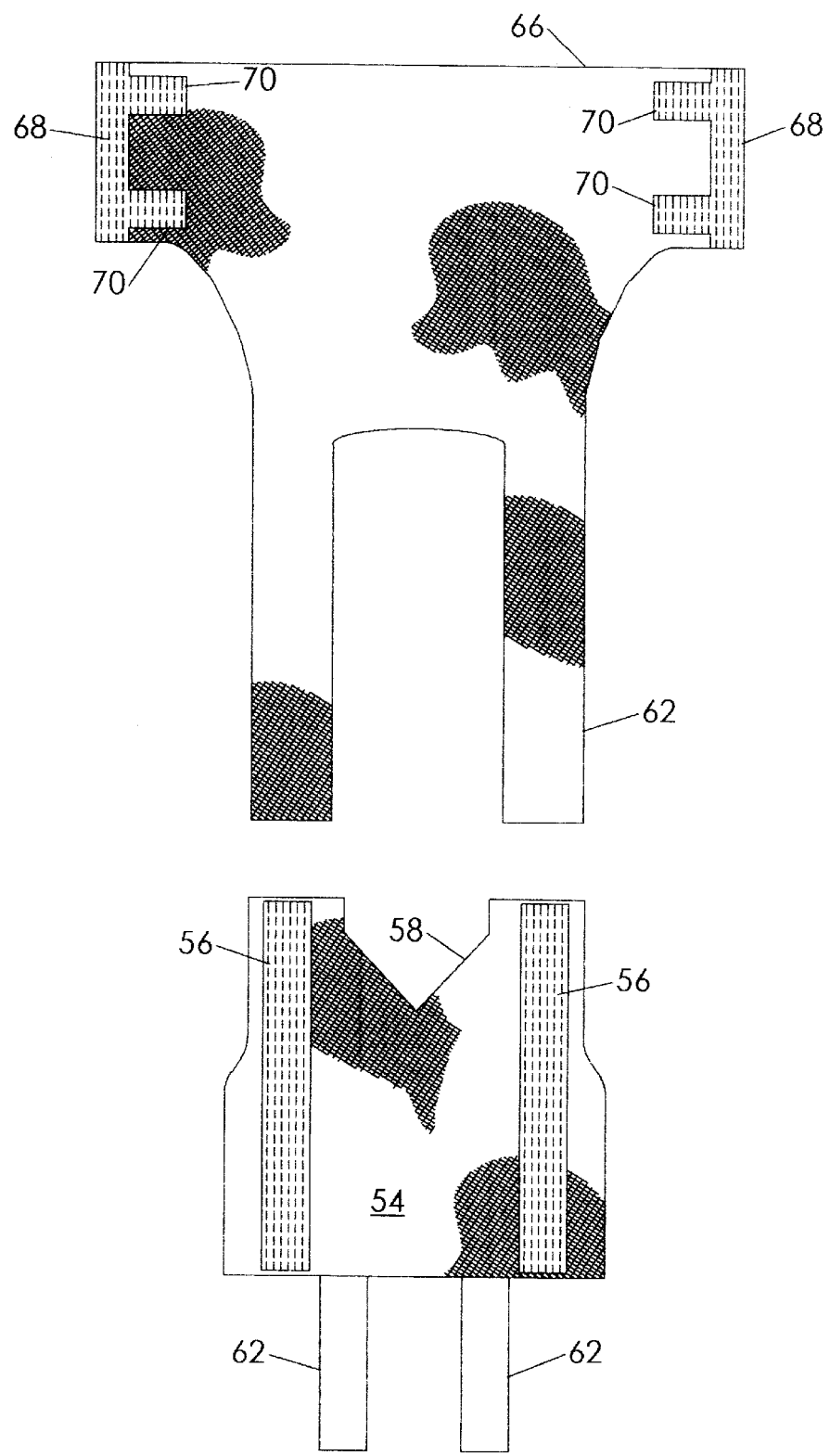
FIG. 4 is a plan view of the inside of the arm-sling vest as in FIG. 3.
Figure 5:
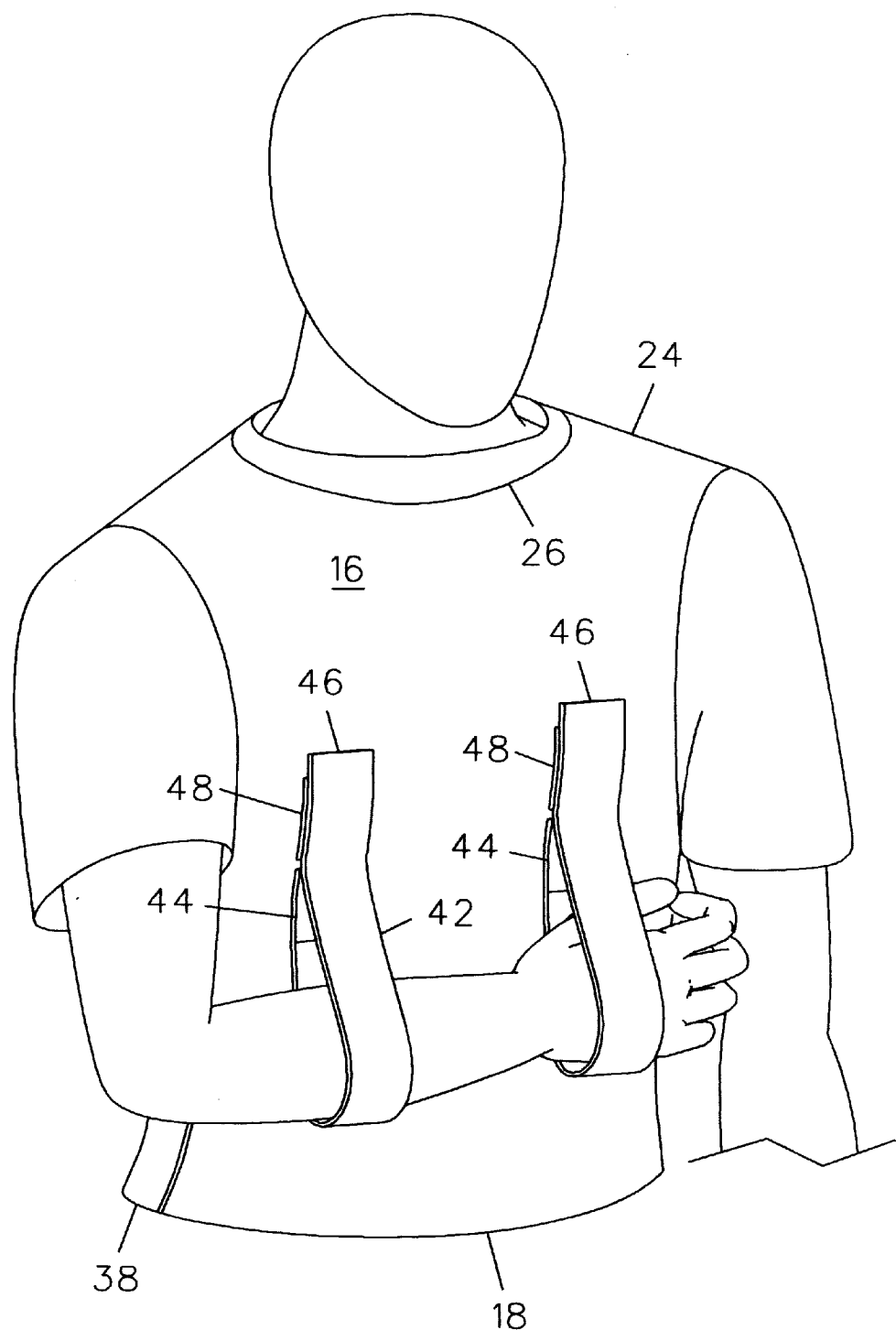
FIG. 5 is a perspective view of the arm-sling vest as in FIG. 1 with a person's forearm being supported in one configuration by the support straps.

Another embodiment of the arm-sling vest 50 is shown in FIGS. 3 and 4 and includes a construction substantially similar to the embodiment described above except as specifically pointed out below. The back vest panel 60 includes a pair of shoulder straps 62 that each have a free end and which define a cutout 63 therebetween (FIG. 3). The cutout 63 extends along substantially the entire length of the shoulder straps 62. The outer surface of each shoulder strap includes a connector strip 64 having one of a hook and loop fastening material. A pair of complementary connector strips 56 are attached to the inner surface 54 of the front vest panel 52 (FIG. 4). Therefore, the front 52 and back 60 vest panels may be releasably connected when the connector strips 64 and complementary connector strips 56 are aligned and engaged. The front vest panel 52 also defines a cutout 58, the cutouts 64, 58 cooperating to permit the front 52 and back 60 vest panels to be fitted over a person's head. Further, the elongate shoulder straps 62 provide overall length-adjustability to the arm-sling vest 50. As shown in FIG. 4, connector strips 68 on the back wing sections 66 include portions 70 perpendicular to the lateral edges thereof. This allows for additional width adjustability and makes the vest more accessible to persons of different sizes or weights.

It is understood that while certain forms of this invention have been illustrated and described, it is not limited thereto except insofar as such limitations are included in the following claims and allowable functional equivalents thereof.

Having thus described the invention, what is claimed as new and desired to be secured by Letters Patent is as follows:

1. An arm-sling vest for stabilizing a human arm, comprising:
   a front vest panel capable of extending over a person's chest and torso;
   a back vest panel connected to said front vest panel and capable of extending over a person's back, said front and back vest panels defining an opening operable to permit said front and back vest panels to be fitted over the head of a person such that said front and back vest panels may be supported upon a person's shoulders;
   means connected to lateral edges of said front and back vest panels for releasably and adjustably fastening said front and back vest panels to one another about a person's torso;
   an elongate first support strap having a first end connected to an outer surface of said front vest panel and a second end depending from a front surface of said front vest panel, one side of said first support strap having a first coupling means mounted longitudinally therealong; and
   a retainer patch fixedly attached to said front surface of said front vest panel and displaced upwardly from said first end of said first support strap, said adjustment patch including a second coupling means that is complementary to said first coupling means, whereby said support strap may be looped about a person's arm and said first and second coupling means may be engaged for stabilizing said person's arm at a desired orientation.

2. The arm-sling vest as in claim 1 wherein said coupling means includes:
   a first pair of connector strips mounted adjacent opposed lateral edges of an inner surface of said back vest portion, each first connector strip having one of a hook and loop fastening material; and
   a second pair of connector strips mounted adjacent opposed lateral edges of said outer surface of said front vest panel, each second connector strip having another of a hook and loop fastening material with respect to said one of a hook and loop fastening material, whereby said front and back vest panels may be adjustably coupled when said first and second pairs of connector strips are engaged.

3. The arm-sling vest as in claim 1 wherein said opening presents a generally annular configuration in said back vest panel and a generally V-shaped configuration in said front vest panel, whereby said front and back vest panels may easily be fitted over a person's head, removed thereover, and is not constrictive about a person's neck.

4. The arm-sling vest as in claim 1 wherein said first and second coupling means are one and the other of hook and loop fastening material, respectively.

5. The arm-sling vest as in claim 1 wherein said first and second coupling means are one and the other of a magnet and metallic material, respectively.

6. The arm-sling vest as in claim 1 wherein said first and second coupling means are snap-fit fasteners.

7. An arm-sling vest for stabilizing a human arm, comprising:
   a front vest panel capable of extending over a person's chest and torso;
   a back vest panel connected to said front vest panel and capable of extending over a person's back, said front and back vest panels defining an opening operable to permit said front and back vest panels to be fitted over the head of a person such that said front and back vest panels may be supported upon a person's shoulders;
   wherein said back vest panel includes a pair of laterally opposed back wing sections, an inner surface of each back wing section having one of a hook and loop fastening material mounted adjacent a lateral edge thereof;
   wherein said front vest panel includes the other of a hook and loop fastening material with respect to said one of a hook and loop fastening material of said wing sections mounted adjacent to respective lateral edges of an outer surface of said front vest panel, whereby said front and back vest panels may be adjustably and releasably coupled by selectively engaging respective hook and loop fastening materials;
   a pair of laterally spaced apart elongate support straps, each support strap having a first end fixedly attached to a front surface of said front vest panel and having a second end depending from said front surface, a front side of each support strap having one of a hook and loop fastening material mounted longitudinally therealong; and
   a pair of retainer patches fixedly attached to said front surface of said front vest panel, said pair of retainer patches being positioned intermediate said opening and respective first ends of said pair of support straps and aligned with a respective imaginary longitudinal axis established by respective support straps, each retainer patch having the other of a hook and loop fastening material with respect to said one of said hook and loop fastening material of respective support straps, whereby a person's forearm may be supported by said pair of support straps by placing said forearm in a generally horizontal configuration and extending said pair of support straps around said forearm so as to cradle said forearm and engaging said hook and loop fastening material of respective support straps and retainer patches.

8. The sling-arm vest as in claim 7 wherein said front vest panel includes a pair of laterally opposed front wing sections substantially coextensive therewith, said other of a hook and loop fastening material with respect to said one of a hook and loop fastening material of said back wing sections being mounted adjacent to respective lateral edges of an outer surface of said front wing sections, whereby to adjustably tighten said sling-arm vest about a person's torso.

9. The arm-sling vest as in claim 7 wherein said opening presents a generally annular configuration in said back vest panel and a generally V-shaped configuration in said front vest panel, whereby said front and back vest panels may easily be fitted over a person's head, removed thereover, and is not constrictive about a person's neck.

10. The arm-sling vest as in claim 7 wherein said front and back vest panels are sleeveless.

11. The arm-sling vest as in claim 7 wherein each of said pair of support straps is independently operable, whereby said forearm may be cradled in user-selectable angular orientations.

12. An arm-sling vest for stabilizing a human arm by supporting the arm using both of a person's shoulders, comprising:

a front vest panel adapted to substantially cover a person's chest and frontal torso, a top edge of said front vest panel defining a first cutout;

a back vest panel having a pair of shoulder straps and defining a second cutout therebetween;

means for releasably coupling said shoulder straps to an upper portion of said front vest panel, said first and second cutouts being cooperatively operable when said shoulder straps and upper portion are connected so as to permit said front and back vest panels to be fitted over the head of a person such that said pair of shoulder straps may be supported upon a person's shoulders;

wherein said back vest panel includes a pair of laterally opposed back wing sections, an inner surface of each back wing section having one of a hook and loop fastening material mounted adjacent a lateral edge thereof;

wherein said front vest panel includes the other of a hook and loop fastening material with respect to said one of a hook and loop fastening material of said wing sections mounted adjacent to respective lateral edges of an outer surface of said front vest panel, whereby said front and back vest panels may be adjustably and releasably coupled by selectively engaging respective hook and loop fastening materials;

a pair of laterally spaced apart elongate support straps, each support strap having a first end fixedly attached to a front surface of said front vest panel and having a second end depending from said front surface, a front side of each support strap having one of a hook and loop fastening material mounted longitudinally therealong; and a pair of retainer patches fixedly attached to said front surface of said front vest panel, said pair of retainer patches being positioned intermediate said opening and respective first ends of said pair of support straps and aligned with a respective imaginary longitudinal axis established by respective support straps, each retainer patch having the other of a hook and loop fastening material with respect to said one of said hook and loop fastening material of respective support straps, whereby a person's forearm may be supported by said pair of support straps by placing said forearm in a generally horizontal configuration and extending said pair of support straps around said forearm so as to cradle said forearm and engaging said hook and loop fastening material of respective support straps and retainer patches.

13. The arm-sling vest as in claim 12 wherein said second cutout extends between said shoulder straps along substantially an entire longitudinal extent thereof and said first cutout presents a generally V-shaped configuration, whereby said front and back vest panels may be fitted over a person's head easily when said shoulder straps are adjusted for persons of different sizes.

14. The arm-sling vest as in claim 12 wherein said means for releasably coupling comprises:

a first pair of connector strips mounted on front surfaces of respective shoulder straps, each of said first pair of connector strips having one of a hook and loop fastening material; and a second pair of spaced apart connector strips mounted on an inner surface of said front vest panel, each of said second pair of connector strips having another of a hook and loop fastening material with respect to said one of a hook and loop fastening material of said first pair of connector strips, whereby said front vest panel and said shoulder straps may be releasably connected at a selected configuration when said first and second pair of connector strips are selectively engaged.

15. The arm-sling vest as in claim 14 wherein said second cutout extends between said shoulder straps along substantially an entire longitudinal extent thereof and said first cutout presents a generally V-shaped configuration, whereby said front and back vest panels may be fitted over a person's head easily when said shoulder straps are adjusted for persons of different sizes.

16. The arm-sling vest as in claim 12 wherein each of said pair of support straps is independently operable, whereby said forearm may be cradled in a plurality of user-selectable angular orientations.

* * * * *